US007214831B2

(12) United States Patent
Lan-Hargest et al.

(10) Patent No.: US 7,214,831 B2
(45) Date of Patent: May 8, 2007

(54) HISTONE DEACETYLASE INHIBITORS BASED ON ALPHA-CHALCOGENMETHYLCARBONYL COMPOUNDS

(75) Inventors: Hsuan-Yin Lan-Hargest, Fallston, MD (US); Robert J. Kaufman, St. Louis, MO (US)

(73) Assignee: Errant Gene Therapeutics, LLC, Phoenix, MD (US)

( * ) Notice: Subject to any disclaimer, the term of this patent is extended or adjusted under 35 U.S.C. 154(b) by 0 days.

(21) Appl. No.: 10/442,191

(22) Filed: May 21, 2003

(65) Prior Publication Data

US 2004/0023944 A1 Feb. 5, 2004

Related U.S. Application Data

(60) Provisional application No. 60/382,077, filed on May 22, 2002.

(51) Int. Cl.
 C07C 323/22 (2006.01)
 C07C 321/10 (2006.01)
 C07C 49/203 (2006.01)
(52) U.S. Cl. .................... 568/42; 568/43; 568/64; 568/308; 568/417
(58) Field of Classification Search ............... 558/253, 558/250; 560/129; 568/20, 42, 43, 308; 568/64, 417; 514/546, 678, 706, 513
 See application file for complete search history.

(56) References Cited

U.S. PATENT DOCUMENTS

| 3,875,232 | A | 4/1975 | Magee |
| 4,966,721 | A | 10/1990 | Farng et al. |
| 5,075,482 | A | 12/1991 | Seltzer et al. |
| 5,523,495 | A | 6/1996 | Oda et al. |
| 5,601,699 | A | 2/1997 | Degnan et al. |
| 5,859,052 | A | 1/1999 | Nugent et al. |
| 5,877,329 | A | 3/1999 | Chen et al. |
| 5,908,868 | A | 6/1999 | Buck et al. |
| 5,925,644 | A | 7/1999 | Jakobi et al. |
| 5,965,719 | A | 10/1999 | Hindsgaul |
| 5,981,580 | A | 11/1999 | Nugent et al. |
| 6,071,923 | A | 6/2000 | Nudelman et al. |
| 6,118,001 | A | * 9/2000 | Owen et al. ............ 546/229 |
| 6,133,296 | A | 10/2000 | Lieb et al. |
| 6,150,567 | A | 11/2000 | Sugawa et al. |
| 6,235,717 | B1 | 5/2001 | Leban et al. |
| 6,255,342 | B1 | 7/2001 | Lieb et al. |
| 6,495,719 | B2 | 12/2002 | Lan-Hargest et al. |
| 2003/0153465 | A1 | 8/2003 | Schallner et al. |

FOREIGN PATENT DOCUMENTS

| AU | 734489 | 12/1998 |
| AU | 764182 | 11/2000 |
| EP | 42298 B1 | 9/1984 |
| EP | 622672 | 11/1994 |
| EP | 1148102 | 10/2001 |
| EP | 1273571 | 8/2003 |
| WO | WO98/22444 | 5/1998 |
| WO | WO00/00469 | 1/2000 |
| WO | WO00/66557 | 11/2000 |
| WO | WO01/36354 | 5/2001 |
| WO | WO01/70675 | 9/2001 |

OTHER PUBLICATIONS

Collins et al., "Oral Sodium Phenylbutyrate Therapy in Homozygous β Thalassemia: A Clinical Trial," Blood, 85(1), 1995, 43-49.
Denney et al., "Preparation and Reactions of Some Phosphobetaines," J. Org. Chem., 27, 1962, 3404-3408.
Fruehauf et al., "Use of the Extreme Drug Resistance Assay to Evaluate Mechanisms of Resistance in Ovarian Cancer: Taxol Resistance and MDR-1 Expression," Chemosensitivity Testing in Gyneologic Malignancies and Breast Cancer, 19, 1994, 39-52.
Grunstein, "Histoneactylation in chromatin structure and transcription," Nature, 389, 1997, 349-352.
Hoffmann et al., "A non-isotopic assay for histone deacetylase activity," Nucleic Acids Research, 27 (9), 1999, 2057-2058.
Kano et al., "New Synthetic Design for Formation of Carbon-Carbon Triple Bonds," J. Org. Chem., 43 (22), 1978, 4366-4367.
Kolle et al., "Biochemical Methods for Analysis of Histone Deacetylases, " METHODS: A Comparison to Methods in Enzymology, 15, 1998, 323-331.
Lebedev et al., "Acylation of Cyclopropyl-Substituted Alkenes with Complexes Formed by ω-(Ethylthio)alkanol Flourides and Boron Trifluoride," Russian Journal of Organic Chemistry, 37(3), 2001, 326-333.
Magdesieva et al., Zh. Org. Khim, 17(2), 1981, 340-342.
Marks et al., "Histone deacetylase inhibitors; inducers of differentiation of apoptosis of transformed cells," (Database Caplus, Accession No. 2000:598231), Journal of the National Cancer Institute, 92(15), 2000, 1210-1216.
Moser et al., "Measurement of Saturated Very Long Chain Fatty Acids in Plasma," Techniques in Diagnostic Human Biochemical Genetics: A Laboratory Manual, 1991, 177-191.
Panyim et al., "High Resolution Acrylamide Gel Electrophoresis of Histones," Archives of Biochemistry and Biophysics, 130, 1969, 337-346.
Parameswara et al., "One-Step Vilsmeier Route to Some 5-Aryl-3-methyl-2(E), 4(E)-pentadienals and thier Oxidation to Penta-dienoic Acids," Synthesis, 1980, 815-818.

(Continued)

*Primary Examiner*—Charanjit S. Aulakh
(74) *Attorney, Agent, or Firm*—Steptoe & Johnson LLP

(57) ABSTRACT

Histone deacetylase is a metallo-enzyme with zinc at the active site. Compounds having a zinc-binding moiety, for example, an alpha-chalcogenmethylcarbonyl group, such as an alpha-ketothio group, can inhibit histone deacetylase. Histone deacetylase inhibition can repress gene expression, including expression of genes related to tumor suppression. Accordingly, inhibition of histone deacetylase can provide an alternate route for treating cancer, hematological disorders, e.g., hemoglobinopathies, autosomal dominant disorders, e.g. spinal muscular atrophy and Huntington's disease, genetic related metabolic disorders, e.g., cystic fibrosis and adrenoleukodystrophy, or for stimulating hematopoietic cells ex vivo.

32 Claims, No Drawings

OTHER PUBLICATIONS

Pazin et al., "What's Up and Down with Histone Deacetylation and Transcription?," Cell, 89, 1997, 325-328.

Steffan et al., "Histone deacetylase inhibitors arrest polyglutamine-dependent neurodegeneration in Drosphila," Nature, 413, 2001, 739-743.

Steinberg, "The acetylation state of nuclear proteins could be one key to pathology and treatment," The Scientist, 16 (2), 2002, 34.

Taguchi et al., "A New Method for the Synthesis of 3-Alkylfuran and 2, 4-Dialkylfuran," Chemistry Letters, 8, 1975, 853-854.

Trager et al., "Human Malaria Parasites in Continuous Culture," Science, 193, 1976, 673-675.

Wade et al., "Histone acetylation: chromatin in action," Trends Biochem. Sci., 22, 1997, 128-132.

Watkins et al., "Peroxisomal Fatty Acid $\beta$-Oxidation in HepG2 Cells," Archives of Biochemistry and Biophysics, 289 (2), 1991, 329-336.

Wolffe, "Histone Deacetylase: A Regulator of Transcription," Science, 272, 1996, 371-372.

E. Corey et al., "t-butoxymethyllithium: direct preparation from t-butyl-methyl ether and applications as hydroxymethyl anion equivalent." *Tetrahedron Letters*. vol. 24, No. 31, 1983, p. 3165-3168.

Carreira et al., "Catalytic, Enantioselective Acetone Aldol Additions with 2-methoxypropene." *Journal of the American Chemical Society*, American Chemical Society, Washington DC, (1995) p. 3649-3650.

\* cited by examiner

HISTONE DEACETYLASE INHIBITORS BASED ON ALPHA-CHALCOGENMETHYLCARBONYL COMPOUNDS

CLAIM OF PRIORITY

This application claims priority under 35 USC § 119(e) to U.S. patent application Ser. No. 60/382,077, filed on May 22, 2002, the entire contents of which is hereby incorporated by reference.

TECHNICAL FIELD

This invention relates to alpha-chalcogenmethylcarbonyl compounds, and more particularly to alpha-chalcogenmethylcarbonyl compounds that are histone deacetylase inhibitors.

BACKGROUND

DNA in the nucleus of the cell exists as a hierarchy of compacted chromatin structures. The basic repeating unit in chromatin is the nucleosome. The nucleosome consists of a histone octamer of proteins in the nucleus of the cell around which DNA is wrapped twice. The orderly packaging of DNA in the nucleus plays an important role in the functional aspects of gene regulation. Covalent modifications of the histones have a key role in altering chromatin higher order structure and function and ultimately gene expression. The covalent modification of histones, such as acetylation, occurs by enzymatically mediated processes.

Regulation of gene expression through the inhibition of the nuclear enzyme histone deacetylase (HDAC) is one of several possible regulatory mechanisms whereby chromatin activity can be affected. The dynamic homeostasis of the nuclear acetylation of histones can be regulated by the opposing activity of the enzymes histone acetyl transferase (HAT) and histone deacetylase (HDAC). Transcriptionally silent chromatin can be characterized by nucleosomes with low levels of acetylated histones. Acetylation reduces the positive charge of histones, thereby expanding the structure of the nucleosome and facilitating the interaction of transcription factors with the DNA. Removal of the acetyl group restores the positive charge, condensing the structure of the nucleosome. Histone acetylation can activate DNA transcription, enhancing gene expression. Histone deacetylase can reverse the process and can serve to repress gene expression. See, for example, Grunstein, *Nature* 389, 349–352 (1997); Pazin et al., *Cell* 89, 325–328 (1997); Wade et al., *Trends Biochem. Sci.* 22, 128–132 (1997); and Wolffe, *Science* 272, 371–372 (1996).

SUMMARY

Histone deacetylase is a metallo-enzyme with zinc at the active site. Compounds having a zinc-binding moiety, for example, an alpha-chalcogenmethylcarbonyl group such as an alpha-ketothio group, can inhibit histone deacetylase. Histone deacetylase inhibition can alter gene expression, including expression of genes related to tumor suppression. Accordingly, inhibition of histone deacetylase can provide an alternate route for treating cancer, hematological disorders, e.g., hemoglobinopathies, genetic related metabolic disorders, e.g., cystic fibrosis and adrenoleukodystrophy, autosomal dominant disorders, e.g. Huntington's disease and spinal muscular atrophy, or for stimulating hematopoietic cells ex vivo.

In one aspect, a compound has formula (I):

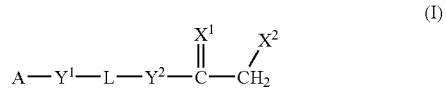

In formula (I), A is a cyclic moiety selected from the group consisting of $C_{3-14}$ cycloalkyl, 3–14 membered heterocycloalkyl, $C_{4-14}$ cycloalkenyl, 3–8 membered heterocycloalkenyl, aryl, or heteroaryl. The cyclic moiety can be optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl. Alternatively, A is a saturated branched $C_{3-12}$ hydrocarbon chain or an unsaturated branched $C_{3-12}$ hydrocarbon chain optionally interrupted by —O—, —S—, —N($R^a$)—, —C(O)—, —N($R^a$)—$SO_2$—, —$SO_2$—N($R^a$)—, —N($R^a$)—C(O)—O—, —O—C(O)—N($R^a$)—, —N($R^a$)—C(O)N($R^b$)—, —O—C(O)—, —C(O)—O—, —O—$SO_2$—, —$SO_2$—O—, or —O—C(O)—O—. Each of $R^a$ and $R^b$, independently, can be hydrogen, alkyl, alkenyl, alkynyl, alkoxy, hydroxylalkyl, hydroxyl, or haloalkyl. Each of the saturated and the unsaturated branched hydrocarbon chain can be optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl.

In formula (I), each of $Y^1$ and $Y^2$, independently, is —$CH_2$—, —O—, —S—, —N($R^c$)—, —N($R^c$)—C(O)—O—, —N($R^c$)—C(O)—, —C(O)—N($R^c$)—, —O—C(O)—N($R^c$)—, —N($R^c$)—C(O)—N($R^d$)—, —O—C(O)—O—, or a bond. Each of $R^c$ and $R^d$, independently, can be hydrogen, alkyl, alkenyl, alkynyl, alkoxy, hydroxylalkyl, hydroxyl, or haloalkyl.

In formula (I), L is a straight $C_{3-12}$ hydrocarbon chain optionally containing at least one double bond, at least one triple bond, or at least one double bond and one triple bond. The hydrocarbon chain can be optionally substituted with $C_{1-4}$ alkyl, $C_{2-4}$ alkenyl, $C_{2-4}$ alkynyl, $C_{1-4}$ alkoxy, hydroxyl, halo, amino, thio, alkylthio, arylthio, aralkylthio, acylthio, nitro, cyano, $C_{3-5}$ cycloalkyl, 3–5 membered heterocycloalkyl, monocyclic aryl, 5–6 membered heteroaryl, $C_{1-4}$ alkylcarbonyloxy, $C_{1-4}$ alkyloxycarbonyl, $C_{1-4}$ alkylcarbonyl, or formyl; and further being optionally interrupted by —O—, —N($R^e$)—, —N($R^e$)—C(O)—O—, —O—C(O)—N($R^e$)—, —N($R^e$)—C(O)—N($R^f$)—, or —O—C(O)—O—. Each of $R^e$ and $R^f$, independently, can be hydrogen, alkyl, alkenyl, alkynyl, alkoxy, hydroxylalkyl, hydroxyl, or haloalkyl.

In formula (I), $X^1$ is O or S and $X^2$ is —$OR^1$, —$SR^1$, or —$SeR^1$. $R^1$ can be hydrogen, alkyl, acyl, aryl or aralkyl. Preferably, $X^1$ is O, $X^2$ is —$SR^1$, $R^1$ is hydrogen, $C_{1-4}$ alkyl, or $C_{1-4}$ acyl, or combinations thereof.

In formula (I), when $Y^1$ is a bond and L is saturated, the carbon adjacent to $Y^1$ is not substituted with $C_{1-4}$ alkoxy or hydroxyl.

In formula (I), in certain circumstances, A is phenyl, $Y^1$ is a bond, and L is a $C_{6-12}$ hydrocarbon chain containing three double bonds and the carbon adjacent to $Y^1$ is substituted with phenyl. In other circumstances, A is phenyl, $Y^1$ is a bond, and L is a $C_{3-12}$ hydrocarbon chain and the carbon adjacent to $Y^1$ is substituted with two phenyls.

In another aspect, a compound has formula (II):

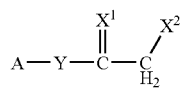
(II)

In formula (II), A is a cyclic moiety selected from the group consisting of $C_{3-14}$ cycloalkyl, 3–14 membered heterocycloalkyl, $C_{4-14}$ cycloalkenyl, 3–8 membered heterocycloalkenyl, aryl, or heteroaryl. The cyclic moiety can be optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl.

In formula (II), Y is a straight C2–12 hydrocarbon chain containing at least one double bond, at least one triple bond, or at least one double bond and one triple bond. The hydrocarbon chain can be optionally interrupted by —O—, —S—, —N($R^a$)—, —C(O)—, —N($R^a$)—$SO_2$—, —$SO_2$—N($R^a$)—, —N($R^a$)—C(O)—O—, —O—C(O)—N($R^a$)—, —N($R^a$)—C(O)—N($R^b$)—, —O—C(O)—, —C(O)—O—, —O—$SO_2$—, —$SO_2$—O—, or —O—C(O)—O—. Each of $R^a$ and $R^b$, independently, can be hydrogen, alkyl, alkenyl, alkynyl, alkoxy, hydroxylalkyl, hydroxyl, or haloalkyl; and being optionally substituted with alkyl, alkenyl, alkynyl, alkoxy, hydroxyl, hydroxylalkyl, halo, haloalkyl, amino, alkylcarbonyloxy, alkyloxycarbonyl, alkylcarbonyl, alkylsulfonylamino, aminosulfonyl, or alkylsulfonyl.

In formula (II), $X^1$ is O or S and $X^2$ is —$OR^1$, or —$SR^1$. $R^1$ can be hydrogen, alkyl, acyl, aryl or aralkyl. Preferably, $X^1$ is O, $X^2$ is —$SR^1$, $R^1$ is hydrogen, $C_{1-4}$ alkyl, or $C_{1-4}$ acyl, or combinations thereof In formula (II), when Y is a $C_2$ hydrocarbon chain having at least one double bond, A is not $C_3$ cycloalkyl.

The compound can be S-(2-oxo-8-phenyl)-3,5,7-octatrienyl thioacetate or S-(2-oxo-8phenoxy)-3,5,7-octatrienyl thioacetate.

In another aspect, a method of inhibiting histone deacetylation activity in cells. The method includes contacting the cells with an effective amount of a compound of formula (I), thereby treating one or more disorders mediated by histone deacetylase or stimulating hematopoietic cells ex vivo, and determining whether the level of acetylated histones in the treated cells is higher than in untreated cells under the same conditions. When used in the method, the compound is of formula (I)

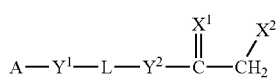
(I)

In the method, A is a cyclic moiety selected from the group consisting of $C_{3-14}$ cycloalkyl, 3–14 membered heterocycloalkyl, $C_{4-14}$ cycloalkenyl, 3–8 membered heterocycloalkenyl, aryl, or heteroaryl. The cyclic moiety can be optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkylcarbonyl, alkylsulfonylamino, aminosulfonyl, or alkylsulfonyl. Alternatively, A is a saturated $C_{1-12}$ hydrocarbon chain or an unsaturated $C_{2-12}$ hydrocarbon chain optionally interrupted by —O—, —S—, —N($R^a$)—, —C(O)—, —N($R^a$)—$SO_2$—, —$SO_2$—N($R^a$)—, —N($R^a$)—C(O)—O—, —O—C(O)—N($R^a$)—, —N($R^a$)—C(O)—N($R^b$)—, —O—C(O)—, —C(O)—O—, —O—$SO_2$—, —$SO_2$—O—, or —O—C(O)—O—. Each of $R^a$ and $R^b$, independently, can be hydrogen, alkyl, alkenyl, alkynyl, alkoxy, hydroxylalkyl, hydroxyl, or haloalkyl. Each of the saturated and the unsaturated branched hydrocarbon chain can be optionally substituted with alkyl, alkenyl, alkynyl, alkoxy, hydroxyl, hydroxylalkyl, halo, haloalkyl, amino, alkylcarbonyloxy, alkyloxycarbonyl, alkylcarbonyl, alkylsulfonylamino, aminosulfonyl, or alkylsulfonyl.

In the method, each of $Y^1$ and $Y^2$, independently, can be —$CH_2$—, —O—, —S—, —N($R^c$)—, —C(O)—, —C(N$OR^c$)—, —N($R^c$)—C(O)—O—, —N($R^c$)—C(O)—, —C(O)—N($R^c$)—, —O—C(O)—N($R^c$)—, —N($R^c$)—C(O)—N($R^d$)—, —O—C(O)—O—, or a bond. Each of $R^c$ and $R^d$, independently, can be hydrogen, alkyl, alkenyl, alkynyl, alkoxy, hydroxylalkyl, hydroxyl, or haloalkyl.

In the method, L is a straight $C_{1-12}$ hydrocarbon chain optionally containing at least one double bond, at least one triple bond, or at least one double bond and one triple bond. The hydrocarbon chain can be optionally substituted with $C_{1-4}$ alkyl, $C_{2-4}$ alkenyl, $C_{2-4}$ alkynyl, $C_{1-4}$ alkoxy, hydroxyl, halo, amino, nitro, cyano, $C_{3-5}$ cycloalkyl, 3–5 membered heterocycloalkyl, monocyclic aryl, 5–6 membered heteroaryl, $C_{1-4}$ alkylcarbonyloxy, $C_{1-4}$ alkyloxycarbonyl, $C_{1-4}$ alkylcarbonyl, or formyl. The hydrocarbon chain can be optionally interrupted by —O—, —N($R^e$)—, —N($R^e$)—C(O)—O—, —O—C(O)—N($R^e$)—, —N($R^e$)—C(O)—N($R^f$)—, or —O—C(O)—O—. Each of $R^e$ and $R^f$, independently, can be hydrogen, alkyl, alkenyl, alkynyl, alkoxy, hydroxylalkyl, hydroxyl, or haloalkyl.

In the method, $X^1$ is O or S and $X^2$ is —$OR^1$, —$SR^1$, or —$SeR^1$. $R^1$ can be hydrogen, alkyl, acyl, aryl or aralkyl. Preferably, $X^1$ is O, $X^2$ is —$SR^1$, $R^1$ is hydrogen or $C_{1-4}$ acyl, or combinations thereof.

In the method, when $Y^1$ is a bond and L is saturated, the carbon adjacent to $Y^1$ is not substituted with $C_{1-4}$ alkoxy or hydroxyl and when $Y^1$ is —C(O)—, —C(N$OR^c$)—, L is not saturated.

In the method, the compound can be ethylene glycol bisthioglycolate, S-(2-oxo-4-phenyl)butyl thioacetate, ethyl 2-mercaptoacetate, S-(2-oxo-8-phenyl)-3,5,7-octatrienyl thioacetate, or S-(2-oxo-8-phenoxy)-3,5,7-octatrienyl thioacetate.

The disorder can be cancer, hemoglobinopathies, thalassemia, sickle cell anemia, cystic fibrosis, protozoan infection, spinal muscular atrophy, Huntington's disease, alpha-1 anti-trypsin, retrovirus gene vector reactivation, wound healing, hair growth, peroxisome biogenesis disorder, or adrenoleukodystrophy.

In certain circumstances, $Y^1$ can be not a bond and L can be a $C_{3-8}$ hydrocarbon chain optionally substituted with $C_{1-2}$ alkyl, $C_{1-2}$ alkoxy, hydroxyl, —$NH_2$, —NH($C_{1-2}$ alkyl), or —N($C_{1-2}$ alkyl)$_2$. In other circumstances, each of $Y^1$ and $Y^2$, independently, can be —$CH_2$—, —O—, —N($R^c$)—, or a bond.

In certain circumstances, L can be a $C_{3-8}$ hydrocarbon chain, a $C_{4-12}$ hydrocarbon chain, a $C_{5-12}$ hydrocarbon chain, a $C_{5-10}$ hydrocarbon chain, or a $C_{6-8}$ hydrocarbon chain. L can be substituted with $C_{1-2}$ alkyl, $C_{1-2}$ alkoxy, hydroxyl, —$NH_2$, —NH($C_{1-2}$ alkyl), or —N($C_{1-2}$ alkyl)$_2$. L can be an unsaturated hydrocarbon chain containing at least one double bond or at least two double bonds. The double bond can be in trans configuration.

In certain circumstances, A can be a $C_{5-8}$ cycloalkenyl, 5–8 membered heteroalkenyl, phenyl, naphthyl, indanyl, or tetrahydronaphthyl. A can be optionally substituted with alkyl alkenyl, alkynyl, alkoxy, hydroxyl, hydroxylalkyl, halo, haloalkyl, or amino.

A salt of any of the compounds can be prepared. For example, a pharmaceutically acceptable salt can be formed when an amino-containing compound of this invention reacts with an inorganic or organic acid. Some examples of such an acid include hydrochloric acid, hydrobromic acid, hydroiodic acid, sulfuric acid, phosphoric acid, p-bromophenylsulfonic acid, carbonic acid, succinic acid, citric acid, benzoic acid, and acetic acid. Examples of pharmaceutically acceptable salts thus formed include sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, and maleate. A compound of this invention may also form a pharmaceutically acceptable salt when a compound of this invention having an acid moiety reacts with an inorganic or organic base. Such salts include those derived from inorganic or organic bases, e.g., alkali metal salts such as sodium, potassium, or lithium salts; alkaline earth metal salts such as calcium or magnesium salts; or ammonium salts or salts of organic bases such as morpholine, piperidine, pyridine, dimethylamine, or diethylamine salts.

It should be recognized that a compound of the invention can contain chiral carbon atoms. In other words, it may have optical isomers or diastereoisomers.

Alkyl is a straight or branched hydrocarbon chain containing 1 to 10 (preferably, 1 to 6; more preferably 1 to 4) carbon atoms. Examples of alkyl include, but are not limited to, methyl, ethyl, propyl, isopropyl, butyl, isobutyl, sec-butyl, tert-butyl, n-pentyl, 2-methylhexyl, and 3-ethyloctyl.

Alkenyl and alkynyl refer to a straight or branched hydrocarbon chain containing 2 to 10 carbon atoms and one or more (preferably, 1–4 or more preferably 1–2) double or triple bonds, respectively. Some examples of alkenyl and alkynyl are allyl, 2-butenyl, 2-pentenyl, 2-hexenyl, 2-butynyl, 2-pentynyl, and 2-hexynyl.

Cycloalkyl is a monocyclic, bicyclic or tricyclic alkyl group containing 3 to 14 carbon atoms. Some examples of cycloalkyl are cyclopropyl, cyclopentyl, cyclohexyl, cycloheptyl, adamantyl, and norbornyl. Heterocycloalkyl is a cycloalkyl group containing at least one heteroatom (e.g., 1–3) such as nitrogen, oxygen, or sulfur. The nitrogen or sulfur may optionally be oxidized and the nitrogen may optionally be quaternized. Examples of heterocycloalkyl include piperidinyl, piperazinyl, tetrahydropyranyl, tetrahydrofuryl, and morpholinyl. Cycloalkenyl is a cycloalkyl group containing at least one (e.g., 1–3) double bond. Examples of such a group include cyclopentenyl, 1,4-cyclohexa-di-enyl, cycloheptenyl, and cyclooctenyl groups. By the same token, heterocycloalkenyl is a cycloalkenyl group containing at least one heteroatom selected from the group of oxygen, nitrogen or sulfur.

Aryl is an aromatic group containing a 5–14 member ring and can contain fused rings, which may be saturated, unsaturated, or aromatic. Examples of an aryl group include phenyl, naphthyl, biphenyl, phenanthryl, and anthracyl. If the aryl is specified as "monocyclic aryl," if refers to an aromatic group containing only a single ring, i.e., not a fused ring.

Heteroaryl is aryl containing at least one (e.g., 1–3) heteroatom such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

The cyclic moiety can be a fused ring formed from two or more of the just-mentioned groups. Examples of a cyclic moiety having fused rings include fluorenyl, dihydrodibenzoazepine, dibenzocycloheptenyl, 7H-pyrazino[2,3-c]carbazole, or 9,10-dihydro-9,10-[2]buteno-anthracene.

Amino protecting groups and hydroxy protecting groups are well-known to those in the art. In general, the species of protecting group is not critical, provided that it is stable to the conditions of any subsequent reaction(s) on other positions of the compound and can be removed without adversely affecting the remainder of the molecule. In addition, a protecting group may be substituted for another after substantive synthetic transformations are complete. Examples of an amino protecting group include, but not limited to, carbamates such as 2,2,2-trichloroethylcarbamate or tertbutylcarbamate. Examples of a hydroxyl protecting group include, but not limited to, ethers such as methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other protecting groups and reaction conditions can be found in T. W. Greene, *Protective Groups in Organic Synthesis*, (3rd, 1999, John Wiley & Sons, New York, N.Y.).

Note that an amino group can be unsubstituted (i.e., —$NH_2$), mono-substituted (i.e., —NHR), or di-substituted (i.e., —$NR_2$). It can be substituted with groups (R) such as alkyl, cycloalkyl, heterocycloalkyl, aryl, heteroaryl, aralkyl, or heteroaralkyl. Halo refers to fluoro, chloro, bromo, or iodo.

Inhibition of a histone deacetylase in a cell is determined by measuring the level of acetylated histones in the treated cells and measuring the level of acetylated histones in untreated cells and comparing the levels. If the level of histone acetylation in the treated cells increases relative to the untreated cells, histone deacetylase has been inhibited.

Some disorders or physiological conditions may be mediated by hyperactive histone deacetylase activity. A disorder or physiological condition that is mediated by histone deacetylase refers to a disorder or condition wherein histone deacetylase plays a role in triggering the onset thereof. Examples of such disorders or conditions include, but not limited to, cancer, hemoglobinopathies (e.g., thalassemia or sickle cell anemia), cystic fibrosis, protozoan infection, spinal muscular atrophy, Huntington's disease, alpha-1 antitrypsin, retrovirus gene vector reactivation, wound healing, hair growth, peroxisome biogenesis disorder, and adrenoleukodystrophy.

Other features or advantages will be apparent from the following detailed description of several embodiments, and also from the appended claims.

DETAILED DESCRIPTION

The compounds of formula (I) and (II) can generally be prepared according to the following methods. The alpha-chalcogenmethylcarbonyls can be prepared from a methyl ketone, as shown in Scheme A. Generally, a methyl ketone can be activated as a silyl enol ether. Next, the silyl enol ether can react with thionyl chloride to form a chloromethyl ketone. The chloromethyl ketone can then react with a chalcogen-containing compound of the formula $X^2H$, where $X^2$ is $-OR^1$, $-SR^1$, or $-SeR^1$ and $R^1$ is hydrogen, alkyl, acyl, aryl or aralkyl. Alternatively, the alpha-chalcogenmethylcarbonyl can be made by converting a carboxylic acid to the corresponding chloromethyl ketone by sequential treatment with oxalyl chloride, diazomethane, and HCl, as summarized in Scheme B. The resulting chloromethyl ketone can then converted to the alpha-chalcogenmethylcarbonyl as shown in Scheme A.

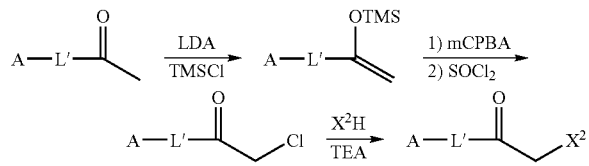

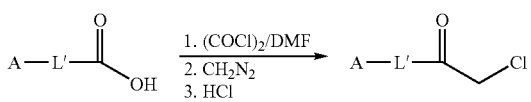

A carboxylic acid-containing compound can be prepared by any known methods in the art. For example, a compound having an unsaturated hydrocarbon chain between A and $-C(=X^1)-$ can be prepared according scheme C:

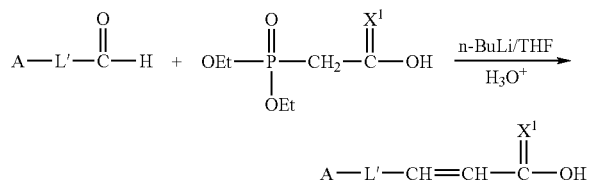

where L' is a saturated or unsaturated hydrocarbon linker between A and $-CH=CH-$ in a compound of the invention, and A and $X^1$ has the same meaning as defined above. See Coutrot et al., Syn. Comm. 133–134 (1978). Briefly, butyllithium is added to an appropriate amount of anhydrous tetrahydrofuran (THF) at a very low temperature (e.g., −65° C.). A second solution having diethylphosphonoacetic acid in anhydrous THF is added dropwise to the stirred butyllithium solution at the same low temperature. The resulting solution is stirred at the same temperature for an additional 30–45 minutes which is followed by the addition of a solution containing an aromatic acrylaldehyde in anhydrous THF over 1–2 hours. The reaction mixture is then warmed to room temperature and stirred overnight. It is then acidified (e.g., with HCl) which allows the organic phase to be separated. The organic phase is then dried, concentrated, and purified (e.g., by recrystallization) to form an unsaturated carboxylic acid.

Alternatively, a carboxylic acid-containing compound can be prepared by reacting an acid ester of the formula A-L'—C(=O)—O-lower alkyl with a Grignard reagent (e.g., methyl magnesium iodide) and a phosphorus oxychloride to form a corresponding aldehyde, which can be further oxidized (e.g., by reacting with silver nitrate and aqueous NaOH) to form an unsaturated carboxylic acid.

Other types of carboxylic acid-containing compounds (e.g., those containing a linker with multiple double bonds or triple bonds) can be prepared according to published procedures such as those described, for example, in Parameswara et al., *Synthesis*, 815–818 (1980) and Denny et al., *J. Org. Chem.*, 27, 3404 (1962). As to compounds wherein $X^1$ is S, they can be prepared according to procedures described in Sandler, S. R. and Karo, W., *Organic Functional Group Preparations*, Volume III (Academic Press, 1972) at pages 436–437. Additional synthetic methods can be found in March, J. *Advanced Organic Chemistry*, 4$^{th}$ ed., (Wiley Interscience, 1992).

Note that appropriate protecting groups may be needed to avoid forming side products during the preparation of a compound of the invention. For example, if the linker L' contains an amino substituent, it can be first protected by a suitable amino protecting group such as trifluoroacetyl or tert-butoxycarbonyl prior to being treated with reagents such as butyllithium. See, e.g., T. W. Greene, supra, for other suitable protecting groups.

A compound produced by the methods shown above can be purified by flash column chromatography, preparative high performance liquid chromatography, or crystallization.

A pharmaceutical composition including the compound described above can be used to inhibit histone deacetylase in cells and can be used to treat disorders associated with abnormal histone deacetylase activity. Some examples of these disorders are cancers (e.g., leukemia, lung cancer, colon cancer, CNS cancer, melanoma, ovarian cancer, cervical cancer, renal cancer, prostate cancer, and breast cancer), hematological disorders (e.g., hemoglobinopathies, thalassemia, and sickle cell anemia) and genetic related metabolic disorders (e.g., cystic fibrosis, spinal muscular atrophy, peroxisome biogenesis disorder, alpha-1 antitrypsin, and adrenoleukodystrophy). The compounds described above can also stimulate hematopoietic cells ex vivo, ameliorating protozoal parasitic infection, accelerate wound healing, and protecting hair follicles.

An effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.* 50, 219 (1966). Body surface area may be approximately determined from height and weight of the patient. See, e.g., *Scientific Tables*, Geigy Pharmaceuticals, Ardsley, N.Y., 537 (1970). An effective amount of a compound described herein can range from about 1 mg/kg to about 300 mg/kg. Effective doses will also vary, as recognized by those skilled in the art, dependent on route of administration, excipient usage, and the possibility of co-usage, pre-treatment, or post-treatment, with other therapeutic treatments including use of other chemotherapeutic agents and radiation therapy. Other chemotherapeutic agents that can be co-administered (either simultaneously or sequentially) include, but not limited to, paclitaxel and its derivatives (e.g., taxotere), doxorubicin, L-asparaginase, dacarbazine, amascrine, procarbazine, hexamethylmelamine, mitoxantrone, and gemicitabine.

The pharmaceutical composition may be administered via the parenteral route, including orally, topically, subcutaneously, intraperitoneally, intramuscularly, and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds. Because some of the compounds described herein can have limited water solubility, a solubilizing agent can be included in the composition to improve the solubility of the compound. For example, the compounds can be solubilized in polyethoxylated castor oil (Cremophor EL®) and may further contain other solvents, e.g., ethanol. Furthermore, compounds described herein can also be entrapped in liposomes that may contain tumor-directing agents (e.g., monoclonal antibodies having affinity towards tumor cells).

A compound described herein can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of a compound described herein with a solid carrier and a lubricant. Examples of solid carriers include starch and sugar bentonite. Compounds of this invention can also be administered in a form of a hard shell tablet or a capsule containing a binder, e.g., lactose or mannitol, a conventional filler, and a tableting agent.

The activities of a compound described herein can be evaluated by methods known in the art, e.g., MTT (3-[4,5-dimehtythiazol-2-yl]-2,5-diphenyltetrazolium bromide) assay, clonogenic assay, ATP assay, or Extreme Drug Resistance (EDR) assay. See Freuhauf, J. P. and Manetta, A., *Chemosensitivity Testing in Gynecologic Malignancies and Breast Cancer* 19, 39–52 (1994). The EDR assay, in particular, is useful for evaluating the antitumor and antiproliferative activity of a compound described herein. Cells are treated for four days with a compound. Both untreated and treated cells are pulsed with tritiated thymidine for 24 hours. Radioactivity of each type of cells is then measured and compared. The results are then plotted to generate drug response curves, which allow $IC_{50}$ values (the concentration of a compound required to inhibit 50% of the population of the treated cells) to be determined.

Histone deacetylase inhibitory activity can be measured based on procedures described by Hoffmann et al., *Nucleic Acids Res.*, 27, 2057–2058 (1999). Briefly, the assay starts with incubating the isolated histone deacetylase enzyme with a compound of the invention, followed by the addition of a fluorescent-labeled lysine substrate (contains an amino group at the side chain which is available for acetylation). HPLC is used to monitor the labeled substrate. The range of activity of each test compound is preliminarily determined using results obtained from HPLC analyses. $IC_{50}$ values can then be determined from HPLC results using different concentrations of compounds of this invention. All assays are duplicated or triplicated for accuracy. The histone deacetylase inhibitory activity can be compared with the increased activity of acetylated histone for confirmation.

Compounds of this invention are also evaluated for effects on treating X-linked adrenoleukodystrophy (X-ALD), a peroxisomal disorder with impaired very long-chain fatty acid (VLCFA) metabolism. In such an assay, cell lines derived from human primary fibroblasts and (EBV-transformed lymphocytes) derived from X-ALD patients grown on RPMI are employed. Tissue culture cells are grown in the presence or absence of test compounds. For VLCFA measurements, total lipids are extracted, converted to methyl esters, purified by TLC and subjected to capillary GC analysis as described in Moser et al., *Technique in Diagnostic Biochemical Genetics: A Laboratory Manual* (ed. A., H.F.) 177–191 (Wiley-Liss, New York, 1991). C24:0 β-oxidation activity of lymphoclastoid cells are determined by measuring their capacity to degrade $[1-^{14}C]$-C24:0 fatty acid to water-soluble products as described in Watkins et al., *Arch. Biochem. Biophys.* 289, 329–336 (1991). The statistical significance of measured biochemical differences between untreated and treated X-ALD cells can be determined by a two-tailed Student's t-test.

Further, compounds of the present invention are evaluated for their effects in treating cystic fibrosis (CF). Since the initial defect in the majority of cases of CF is the inability of mutant CF protein (CFTR) to fold properly and exit the ER, compounds of the invention are tested to evaluate their efficacy in increasing the trafficking of the CF protein out of the ER and its maturation through the Golgi. During its biosynthesis, CFTR is initially synthesized as a nascent polypeptide chain in the rough ER, with a molecular weight of around 120 kDa (Band A). It rapidly receives a core glycosylation in the ER, giving it a molecular weight of around 140 kDa (Band B). As CFTR exits the ER and matures through the Golgi stacks, its glycosylation is modified until it achieves a terminal mature glycosylation, affording it a molecular weight of around 170 kDa (Band C). Thus, the extent to which CFTR exits the ER and traverses the Golgi to reach the plasma membrane may be reflected in the ratio of Band B to Band C protein. CFTR is immunoprecipitated from control cells, and cells exposed to test compounds. Both wt CFTR and ΔF508 CFTR expressing cells are tested. Following lysis, CFTR is immunoprecipitated using various CFTR antibodies. Immunoprecipitates are then subjected to in vitro phosphorylation using radioactive ATP and exogenous protein kinase A. Samples are subsequently solubilized and resolved by SDS-PAGE. Gels are then dried and subject to autoradiography and phosphor image analysis for quantitation of Bands B and C are determined on a BioRad personal fix image station.

Furthermore, compounds of this invention can be used to treat homozygous β thalassemia, a disease in which there is inadequate production of β globin leading to severe anemia. See Collins et al., *Blood,* 85(1), 43–49 (1995).

Still further, compounds of the present invention are evaluated for their use as antiprotozoal or antiparasitic agents. The evaluation can be conducted using parasite cultures (e.g., Asexual *P. falciparum*). See Trager, W. & Jensen, J. B., *Science* 193, 673–675 (1976). Test compounds are dissolved in dimethyl sulfoxide (DMSO) and added to wells of a flat-bottomed 96-well microtitre plate containing human serum. Parasite cultures are then added to the wells, whereas control wells only contain parasite cultures and no test compound. After at least one invasion cycle, and addition of labeled hypoxanthine monohydrochloride, the level of incorporation of labeled hypoxanthine is detected. $IC_{50}$ values can be calculated from data using a non-linear regression analysis.

The toxicity of a compound described herein is evaluated when a compound of the invention is administered by single intraperitoneal dose to test mice. After administration of a predetermined dose to three groups of test mice and untreated controls, mortality/morbidity checks are made daily. Body weight and gross necropsy findings are also monitored. For reference, see Gad, S. C. (ed.), *Safety Assessment for Pharmaceuticals* (Van Nostrand Reinhold, New York, 1995).

The following specific examples, which described syntheses, screening, and biological testing of various compounds of this invention, are therefore, to be construed as merely illustrative, and not limitative of the remainder of the disclosure in any way whatsoever. All publications recited herein, including patents, are hereby incorporated by reference in their entirety.

EXAMPLES

Synthesis of 1-hydroxy-4-phenyl-2-butanone

A solution of 12.33 mL of diisopropylamine in 100 mL of THF was cooled to −25° C. and treated with 8.8 mL of 10M n-butyllithium. After 10 minutes, 12 mL of benzylacetone in 100 mL of THF was added. After 10 minutes, 18.3 mL of chlorotrimethylsilane was added quickly. The resulting mixture was warmed to room temperature and stirred for 2.5 hours. The solution was diluted with pentane (200 mL), washed with cold saturated sodium bicarbonate, dried over sodium sulfate and concentrated in vacuo to afford 18.1 g of a clear yellow liquid which by NMR was perfect for the desired product. The GCMS indicated the presence of both isomers.

Meta-chloroperbenzoic acid (mCPBA, 85%) was added portionwise to a solution of 2-((trimethylsilyl)oxy)-4-phenylbut-1-ene (8.8 g) in 300 mL of dichloromethane at 0° C. The temperature rose to 6° C. The reaction mixture was stirred in an ice bath for 30 minutes, then warmed to room temperature and stirred for an additional two hours. A white precipitate formed initially at low temperature but dissolved upon warming. After two hours at ambient temperature, the mixture was analyzed by GC which showed that all of the silylenol ether had reacted. GCMS showed an m/e of 236 for the desired enol ether epoxide. The reaction mixture was washed with 100 mL of saturated sodium sulfite and twice with 100 mL of saturated sodium bicarbonate and concentrated in vacuo. The residue was dissolved in 40 mL of 1 M tetrabutyl ammonium fluoride in THF and stirred for 45 minutes. The was a slight exotherm. The reaction mixture was concentrated in vacuo then partitioned between 300 mL of methylene chloride and 100 mL of water. The methylene chloride layer was washed with 100 mL of saturated sodium bicarbonate, dried over sodium sulfate and concentrated in vacuo to afford 6.8 g of a brown oil.

GCMS and NMR of the brown oil indicated that both hydroxyketones had been formed although the 1-hydroxy was the major product. The crude oil was chromatograhped on a Biotage 40M using 4:1 hexane:ethyl acetate. The crude oil was loaded on the coumn with 10 mL of 1:1 ethyl acetate:hexanes. Fractions 9–11 contained the starting 4-phenyl-2-butanone. Fraction 20–24 contained ca. 0.3 g (4.6%) of 3-hydroxy-4-phenyl-2-butanone based on the NMR. Fractions 28–29 appeared to be cross contaminated with some of the 3-hydroxyketone by TLC so they were separately isolated to give 0.3 g of slightly impure 1-hydroxy-4-phenyl-2-butanone. Fractions 30–49 contained the pure product (1.6 g, 24%). The proton and carbon NMR spectra matched that expected for the desired product. The synthesis is summarized in Scheme I.

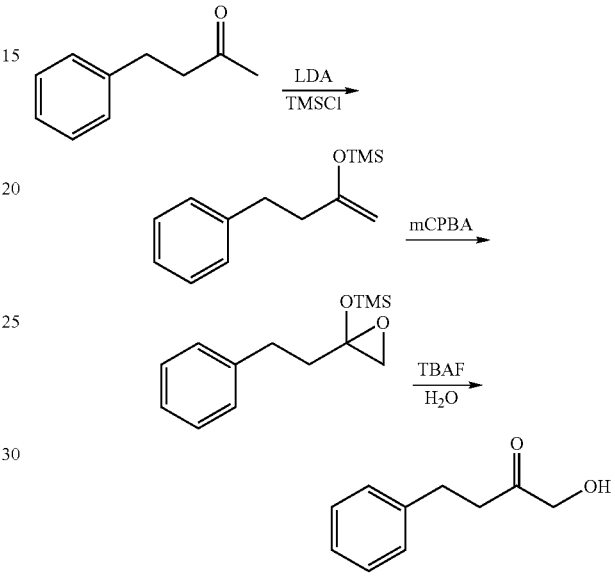

Synethesis of S-(2-oxo-4-phenyl)butyl thioacetate 1-hydroxy-4-phenyl-2-butanone prepared as described above was dissolved in 10 mL of chloroform, cooled to 0–5° C. in an ice bath, then treated with 0.3 mL of thionyl chloride. The reaction was allowed to warm to room temperature and was stirred overnight at room temperature. The reaction mixture became dark and there was obvious gas evolution.

An aliquot was concentrated in vacuo and analyzed by NMR. The product had a spectrum consistent with the desired chloroketone. GCMS of the sample gave an m/e of 182 with the 3:1 chloride isotope ratio (182:184). The GC indicated that there was one major product. This material was used without further purification.

1-chloro-4-phenyl-2-butanone (about 0.44 g) was dissolved in 5 mL of DMF containing 0.2 mL thiolacetic acid. Triethylamine (0.4 mL) was added in a bolus and the resulting mixture was stirred at room temperature and monitored by GC and NMR. There was an exotherm and immediate salt precipitation. An aliquot was analyzed by GC and GCMS. The GC indicated a single new product and the GCMS showed an m/e of 222. The aliquot was also analyzed by NMR and found to be the desired product. The reaction mixture was filtered and the filtrate washed with 25 mL of ethyl acetate. The filtrate was partitioned between 25 mL of ethyl acetate and 15 mL of water. The ethyl acetate layer was washed with 15 mL each of 5% hydrochloric acid, saturated sodium bicarbonate and brine, dried over sodium sulfate and concentrated in vacuo to afford 0.4 g of a dark oil.

The oil was chromatographed on a Biotage 40S column using 1:1 chloroform:hexanes. Fraction 55 began to show product and at fraction 65 the elution solvent was changed to 60:40 chloroform:hexanes. Fractions 66:81 were combined and analyzed by NMR and GC and found to be about 50 mg of the desired product, S-(2-oxo-4-phenyl)butyl thioacetate, in 91% purity. Fractions 82–113 were combined and analyzed by GC and NMR and found to be 43 mg of the desired product in 95% purity. The synthesis is summarized in Scheme II.

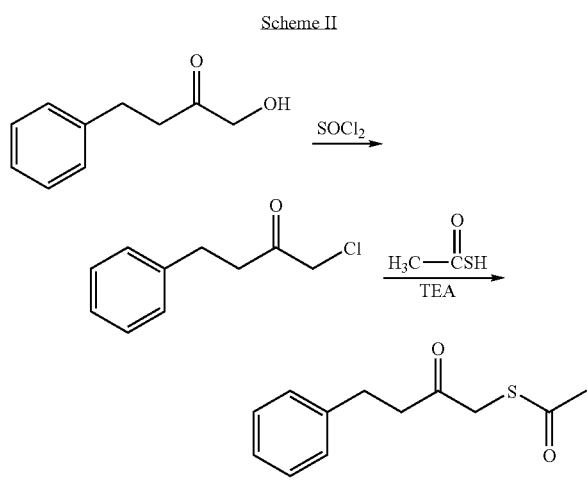

Synthesis of 5-phenyl-2,4-pentadienal

To a cooled (0–5° C.) 927 mL of 1 M solution of phenyl magnesium bromide in tetrahydrofuran was added dropwise a solution of crotonaldehyde (65.0 g) in 130 mL of anhydrous ether over a period of 2 hours and 45 minutes. The reaction was stirred for an additional 45 minutes and then warmed to room temperature. After four more hours of stirring, saturated ammonium chloride aqueous solution (750 mL) was added to the reaction. The mixture was extracted with 750 mL of ether twice. The combined extract was dried over anhydrous potassium carbonate and filtered. The solvent was evaporated to give 135.88 g (99.9%) of the desired 1-phenyl-2-buten-1-ol as an oil which was used in the next step without further purification.

1-Phenyl-2-buten-1-ol (135.88 g) was dissolved in 2300 mL of dioxane and treated with 2750 mL of dilute hydrochloric acid (2.3 mL of concentrated hydrochloric acid in 2750 mL of water) at room temperature. The mixture was stirred overnight and then poured into 4333 mL of ether and neutralized with 2265 mL of saturated aqueous sodium bicarbonate. The aqueous phase was extracted with 1970 mL of ether. The combined extract was dried over anhydrous potassium carbonate. Evaporation of the solvent followed by Kugelrohr distillation at 30° C. for 30 minutes afforded 131.73 g (96.8%) of the desired 4-phenyl-3-buten-2-ol as an oil which was used in the next step without further purification.

Dimethylformamide (DMF, anhydrous, 14 mL) was cooled to 0–5° C. and phosphorus oxychloride (8.2 mL) was added dropwise over a period of 40 minutes. The resulting solution was added dropwise to a cooled (0–5° C.) solution of 4-phenyl-3-buten-2-ol (10 g) in 32 mL of anhydrous DMF over a period of an hour. The reaction mixture was warmed to room temperature over a 35-minute period and then gradually heated up to 80° C. over a period of 45 minutes. The reaction was stirred at 80° C. for three hours and then cooled to 0–5° C. To the cooled reaction solution was added dropwise a solution of sodium acetate (40 g) in deionized water (100 mL) over a period of one hour. The mixture was then reheated to 80° C., stirred at 80° C. for an additional 10 minutes, cooled down to room temperature and extracted with ether (100 mL) twice. The combined extract was washed with brine (100 mL), dried over anhydrous sodium sulfate, filtered and concentrated under vacuum to yield 8.78 g of the desired 5-phenyl-2,4-pentadienal as a liquid which was used in the next step without further purification. $^1$H NMR (CDCl$_3$, 300 MHz), δ(ppm) 7.51 (m, 2H), 7.37 (m, 3H), 7.26 (m, 1H), 7.01 (m, 2H), 6.26 (m, 1H). The synthesis is summarized in Scheme III.

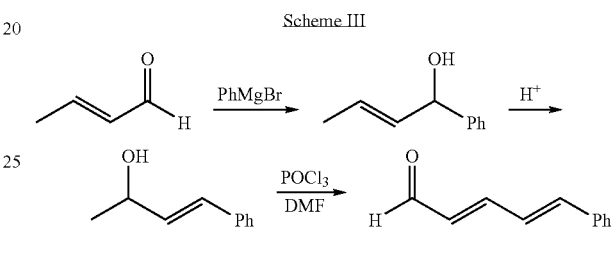

Synthesis of 5-phenoxy-2,4-pentadienal

2-Formylvinyl phenyl ether is prepared by treating phenoxyacetaldehyde with formaldehyde and diethylamine hydrochloride salt. The ether is then reacting with a solution of diethylphosphonoacetic acid and n-butyllithium in anhydrous tetrahydrofuran (THF) to form 5-phenoxy-2,4-pentadienoic acid. 5-Phenoxy-2,4-pentadienal is obtained by first converting the carboxylic acid to a Weinreb amide using oxalyl chloride followed by N,O-dimethylhydroxylamine. Subsequently, reduction of the Weinreb amide with lithium aluminum hydride (LAH) in THF leads to the formation of 5-phenoxy-2,4-pentadienal. The synthesis is summarized in Scheme IV:

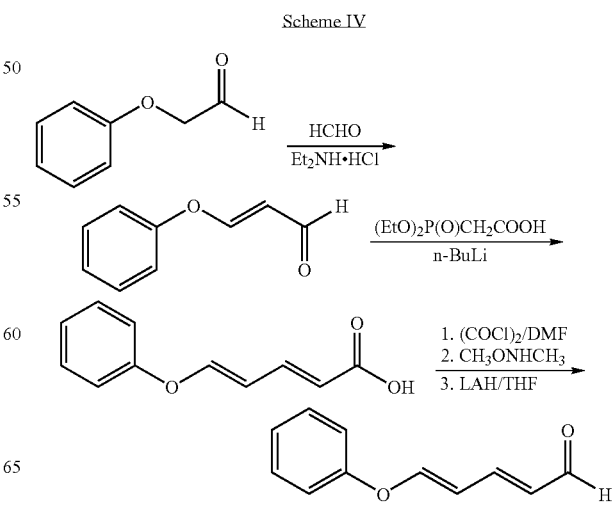

Synthesis of S-(2-oxo-8-phenyl)-3,5,7-octatrienyl thioacetate

S-(2-oxo-8-phenyl)-3,5,7-octatrienyl thioacetate is prepared as outlined in Scheme VA. 8-Phenyl-3,5,7-octatrien-2-one is made by reacting 5-phenyl-2,4-pentadienal in THF with an equal amount of acetic acid and piperidine followed by addition of acetone at room temperature under nitrogen. Treatment of 8-phenyl-3,5,7-octatrien-2-one with lithium diisopropylamide (LDA) and trimethylsilyl chloride (TMSCl) followed by m-chloroperbenzoic acid (mCPBA) leads to the formation of the alpha-keto alcohol. The alcohol is converted to the corresponding chloride by reacting with thionyl chloride. Subsequently, treatment of the resulting chloride with thiolacetic acid in the presence of triethylamine (TEA) give rise to S-(2-oxo-8-phenyl)-3,5,7-octatrienyl thioacetate.

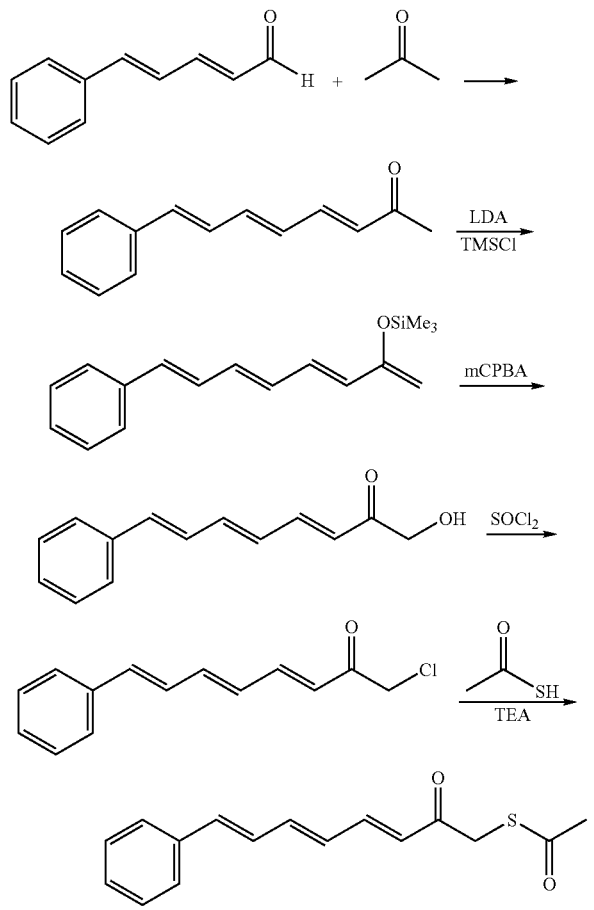

Alternatively, as shown in Scheme VI, S-(2-oxo-8-phenyl)-3,5,7-octatrienyl thioacetate is made by converting 7-phenyl-2,4,6-heptatrienoic acid to the corresponding chloromethyl ketone by addition of oxalyl chloride dropwise in DMF followed by diazomethane and then treatment of HCl. The resulting chloromethyl ketone is treated with thiolacetic acid to form S-(2-oxo-8-phenyl)-3,5,7-octatrienyl thioacetate.

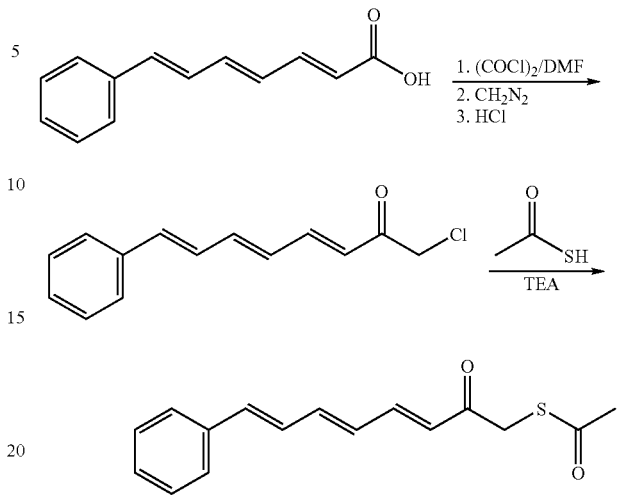

Synthesis of S-(2-oxo-8-phenoxy)-3,5,7-octatrienyl thioacetate

S-(2-oxo-8-phenoxy)-3,5,7-octatrienyl thioacetate is prepared in a similar manner, as shown in Scheme VB.

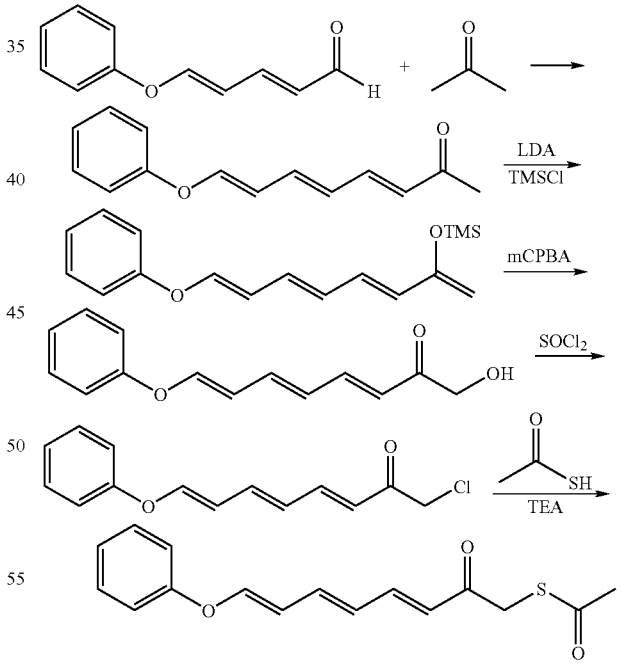

Assays

Compounds selected from ethylene glycol bisthioglycolate, ethyl 2-mercaptoacetate (each of which is commercially available from Sigma-Aldrich), S-(2-oxo-4-phenyl) butyl thioacetate, S-(2-oxo-8-phenyl)-3,5,7-octatrienyl thioacetate, and S-(2-oxo-8-phenoxy)-3,5,7-octatrienyl thioacetate are used in the assays described below.

In Vitro Efficacy Studies—Extreme Drug Resistance (EDR) Assay

The PC3 cell line is maintained in RPMI supplemented with 10% fetal calf serum and antibiotics. Cells are suspended in 0.12% soft agar in complete medium and plated (2,000 cells per well) in different drug concentrations onto a 0.4% agarose underlayer in 24-well plates. Plating calls on agarose underlayers supports the proliferation only of the transformed cells, ensuring that the growth signal stems from the malignant component of the tumor.

All compounds are dissolved in DMSO to 200× stock solutions. Stock solutions are diluted to 20× working solutions using the tissue culture medium, then are serially diluted and added to the 24-well plates. The initial range of concentrations is 1 micromolar to 200 micromolar. No significant changes in pH of the culture medium are observed under the above conditions. Diluent control wells contain PC3 cells treated with DMSO, at the dilutions used for appropriate drug treatment. All experimental points are represented by two separate wells (duplicates). Four wells containing tumor cells that are not treated with drugs serve as negative controls in each experiment.

Cells are incubated with drugs under standard culture conditions for 5 days. Cultures are pulsed with tritiated thymidine ($^3$H-TdR, New Life Science Products, Boston, Mass.) at 5 μCi per well for the last 48 hours of the culture period. Cell culture plates are then heated to 90° C. to liquefy the agarose, and cells are harvested onto glass fiber filters, which are then placed into counting vials containing liquid scintillation fluid. The radioactivity trapped on the filters is counted with a Beckman scintillation counter. The fraction of surviving cells is determined by comparing $^3$H-TdR incorporation in treated (experimental points) and untreated (negative control) wells. Microsoft Excel is used to organize the raw data on EDR experiments, and the SigmaPlot program is utilized to generate drug response curves. All drug response curves are approximated as sigmoidal equations (characteristic for typical drug response curves) to fit the data. $IC_{50}$ values are determined using the approximated sigmoidal curves and expressed as μM.

Histone (Hyper)Acetylation Assay

The effect of a compound described herein on histone acetylation can be evaluated in an assay using mouse erythroleukemia cells. Studies are performed with the DS19 mouse erythroleukemia cells maintained in RPMI 1640 medium with 25 mM HEPES buffer and 5% fetal calf serum. The cells are incubated at 37° C.

Histones are isolated from cells after incubation for periods of 2 and 24 hours. The cells are centrifuged for 5 minutes at 2000 rpm in the Sorvall SS34 rotor and washed once with phosphate buffered saline. The pellets are suspended in 10 mL lysis buffer (10 mM Tris, 50 mM sodium bisulfite, 1% Triton X-100, 10 mM magnesium chloride, 8.6% sucrose, pH 6.5) and homogenized with six strokes of a Teflon pestle. The solution is centrifuged and the pellet washed once with 5 mL of the lysis buffer and once with 5 mL 10 mM Tris, 13 mM EDTA, pH 7.4. The pellets are extracted with 2×1 mL 0.25 N HCl. Histones are precipitated from the combined extracts by the addition of 20 mL acetone and refrigeration overnight. The histones are pelleted by centrifuging at 5000 rpm for 20 minutes in the Sorvall SS34 rotor. The pellets are washed once with 5 mL acetone and protein concentration are quantitated by the Bradford procedure.

Separation of acetylated histones is usually performed with an acetic acid-urea polyacrylamide gel electrophoresis procedure. Resolution of acetylated H4 histones is achieved with 6.25 N urea and no detergent as originally described by Panyim and Chalkley, *Arch. Biochem. Biophys.* 130, 337–346 (1969). 25 μg Total histones are applied to a slab gel which is run at 20 mA. The run is continued for a further two hours after the Pyronin Y tracking dye has run off the gel. The gel is stained with Coomassie Blue R. The most rapidly migrating protein band is the unacetylated H4 histone followed by bands with 1, 2, 3 and 4 acetyl groups which can be quantitated by densitometry. The procedure for densitometry involves digital recording using the Alpha Imager 2000, enlargement of the image using the PHOTOSHOP program (Adobe Corp.) on a MACINTOSH computer (Apple Corp.), creation of a hard copy using a laser printer and densitometry by reflectance using the Shimadzu CS9000U densitometer. The percentage of H4 histone in the various acetylated states is expressed as a percentage of the total H4 histone.

The concentration of a compound of the invention required to decrease the unacetylated H4 histone by 50% (i.e., $EC_{50}$) can then be determined from data obtained using different concentrations of test compounds.

Histone Deacetylation Assay

The determination of the inhibition of histone deacetylase by compounds described herein is based upon the procedure described by Hoffmann et al., *Nucleic Acids Res.* 27, 2057–2058 (1999). The histone deacetylase is isolated from rat liver as previously described in Kolle, D. et al. *Methods. A Companion to Methods in Enzymology* 15: 323–331 (1998). Compounds are initially dissolved in either ethanol or in DMSO to provide a working stock solution. The synthetic substrate used in the assay is N-(4-methyl-7-coumarinyl)-N-α(tert-butyloxy-carbonyl)-N-Ω-acetyll-ysineamide (MAL).

The assay is performed in a final total volume of 120 μL consisting of 100 μL of 15 mM tris-HCl buffer at pH 7.9 and 0.25 mM EDTA, 10 mM NaCl, 10% glycerol, 10 mM mercaptoethanol and the enzyme. The assay is initiated upon the addition of 10 μL of a test compound followed by the addition of a fluorescent-labeled lysine substrate to each assay tube in an ice bath for 15 minutes. The tubes are transferred to a water bath at 37° C. for an additional 90 minutes.

An initial assay is performed to determine the range of activity of each test compound. The determination of $IC_{50}$ values is made from the results of five dilutions in range according to the expected potency for each test compound. Each assay is duplicated or triplicated.

Other embodiments are within the scope of the following claims.

What is claimed is:
1. A compound having the formula (I):

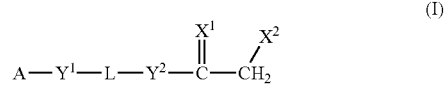

wherein
A is a cyclic moiety selected from the group consisting of aryl; the cyclic moiety being optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl;

each of $Y^1$ and $Y^2$, independently, is a bond;

L is a straight $C_{3-12}$ hydrocarbon chain containing at least one double bond, at least one triple bond, or at least one double bond and one triple bond; the hydrocarbon chain being optionally substituted with $C_{1-4}$ alkyl, $C_{2-4}$ alkenyl, $C_{2-4}$ alkynyl, halo, amino, thio, alkylthio, arylthio, aralkylthio, acylthio, nitro, cyano, $C_{3-5}$ cycloalkyl, 3–5 membered heterocycloalkyl, monocyclic aryl, 5–6 membered heteroaryl, $C_{1-4}$ alkylcarbonyloxy, $C_{1-4}$ alkyloxycarbonyl, $C_{1-4}$ alkylcarbonyl, or formyl; and further being optionally interrupted by —O—, —N($R^e$)—, —N($R^e$)—C(O)—O—, —O—C(O)—N($R^e$)—, —N($R^e$)—C(O)—N($R^f$)—, or —O—C(O)—O—; each of $R^e$ and $R^f$, independently, being hydrogen, alkyl, alkenyl, alkynyl, alkoxy, hydroxylalkyl, hydroxyl, or haloalkyl;

$X^1$ is O or S; and $X^2$ is —OR$^1$, —SR$^1$, or —SeR$^1$, wherein R$^1$ is hydrogen, alkyl, acyl, unsubstituted phenyl or aralkyl;

or a salt thereof.

2. A compound having the formula (II):

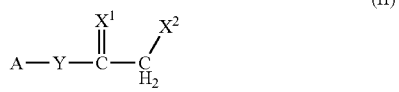

(II)

wherein

A is a cyclic moiety selected from the group consisting of aryl; the cyclic moiety being optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl;

Y is a straight $C_{2-12}$ hydrocarbon chain containing at least one double bond, at least one triple bond, or at least one double bond and one triple bond; the hydrocarbon chain being optionally interrupted by —O—, —S—, —N($R^a$)—, —C(O)—, —N($R^a$)—SO$_2$—, —SO$_2$—N($R^a$)—, —N($R^a$)—C(O)—O—, —O—C(O)—N($R^a$)—, —N($R^a$)—C(O)—N($R^b$)—, —O—C(O)—, —C(O)—, —O—SO$_2$—, —SO$_2$—O—, or —O—C(O)—O—, where each of $R^a$ and $R^b$, independently, is hydrogen, alkyl, alkenyl, alkynyl, alkoxy, hydroxylalkyl, hydroxyl, or haloalkyl; and being optionally substituted with alkyl, alkenyl, alkynyl, alkoxy, hydroxyl, hydroxylalkyl, halo, haloalkyl, amino, alkylcarbonyloxy, alkyloxycarbonyl, alkylcarbonyl, alkylsulfonylamino, aminosulfonyl, or alkylsulfonyl;

$X^1$ is O or S; and $X^2$ is —OR$^1$, or —SR$^1$, wherein R$^1$ is hydrogen, alkyl, acyl, aryl or aralkyl;

or a salt thereof.

3. The compound of claim 1, wherein $X^1$ is O.

4. The compound of claim 1, wherein $X^2$ is SR$^1$.

5. The compound of claim 1, wherein $X^1$ is O and $X^2$ is SR$^1$.

6. The compound of claim 1, wherein L is a $C_{3-8}$ hydrocarbon chain substituted with $C_{1-2}$ alkyl, —NH$_2$, —NH($C_{1-2}$ alkyl), or —N($C_{1-2}$ alkyl)$_2$.

7. The compound of claim 1, wherein L is a $C_{4-12}$ hydrocarbon chain.

8. The compound of claim 1, wherein L is a $C_{5-12}$ hydrocarbon chain.

9. The compound of claim 1, wherein L is a $C_{5-10}$ hydrocarbon chain.

10. The compound of claim 1, wherein L is a $C_{6-8}$ hydrocarbon chain.

11. The compound of claim 5, wherein L is a $C_{5-10}$ hydrocarbon chain.

12. The compound of claim 1, wherein L is an unsaturated hydrocarbon chain containing at least one double bond.

13. The compound of claim 12, wherein the double bond is in trans configuration.

14. The compound of claim 5, wherein L is an unsaturated hydrocarbon chain containing at least one double bond.

15. The compound of claim 14, wherein the double bond is in trans configuration.

16. The compound of claim 1, wherein L is an unsaturated hydrocarbon chain containing at least two double bonds.

17. The compound of claim 5, wherein L is an unsaturated hydrocarbon chain containing at least two double bonds.

18. The compound of claim 1, wherein A is a phenyl, naphthyl, or tetrahydronaphthyl optionally substituted with alkyl alkenyl, alkynyl, alkoxy, hydroxyl, hydroxylalkyl, halo, haloalkyl, or amino.

19. The compound of claim 5, wherein A is a phenyl, naphthyl, or tetrahydronaphthyl optionally substituted with alkyl alkenyl, alkynyl, alkoxy, hydroxyl, hydroxylalkyl, halo, haloalkyl, or amino.

20. The compound of claim 1, wherein the compound is S-(2-oxo-8-phenyl)-3,5,7-octatrienyl thioacetate or S-(2-oxo-8-phenoxy)-3,5,7-octatrienyl thioacetate.

21. The compound of claim 1, wherein A is phenyl, and L is a $C_{6-12}$ hydrocarbon chain containing three double bonds and the carbon adjacent to $Y^1$ is substituted with phenyl.

22. The compound of claim 5, wherein A is phenyl, and L is a $C_{6-12}$ hydrocarbon chain containing three double bonds and the carbon adjacent $Y^1$ is substituted with phenyl.

23. The compound of claim 1, wherein A is phenyl, and L is a $C_{3-12}$ hydrocarbon chain and the carbon adjacent to $Y^1$ is substituted with two phenyl groups.

24. The compound of claim 5, wherein A is phenyl, and L is a $C_{3-12}$ hydrocarbon chain and the carbon adjacent to $Y^1$ is substituted with two phenyl groups.

25. A compound having the formula (I):

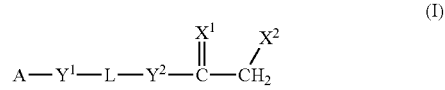

(I)

wherein

A is a cyclic moiety selected from the group consisting of aryl; the cyclic moiety being optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl;

each of $Y^1$ and $Y^2$, independently, is a bond;

L is an unsaturated $C_{2-12}$ hydrocarbon chain containing at least one double bond, at least one triple bond, or at least one double bond and one triple bond; the hydrocarbon chain being optionally interrupted by —O—, —S—, —N($R^a$)—, —C(O)—, —N($R^a$)—SO$_2$—, —SO$_2$—N($R^a$)—, —N($R^a$)—C(O)—O—, —O—C (O)—N(R$^a$)—, —N(R$^a$)—C(O) (—N(R$^b$)—, —O—C(O)—, —C(O)—O—, —O—SO$_2$—, —SO$_2$—O—, or —O—C(O)—O—, where each of R$^a$ and R$^b$, independently, is hydrogen, alkyl, alkenyl, alkynyl, alkoxy, hydroxylalkyl, hydroxyl, or haloalkyl; and being optionally substituted with alkyl, alkenyl, alkynyl, alkoxy, hydroxyl, hydroxylalkyl, halo, haloalkyl, amino, alkylcarbonyloxy, alkyloxycarbonyl, alkylcarbonyl, alkylsulfonylamino, aminosulfonyl, or alkylsulfonyl;

X$^1$ is O or S; and x$^2$ is —OR$^1$, —SR$^1$, or —SeR$^1$, wherein R$^1$ is unsubstituted phenyl;

or a salt thereof.

26. The compound of claim 25, wherein L is an unsaturated C$_{4-12}$ hydrocarbon chain.

27. The compound of claim 25, wherein L is an unsaturated C$_{5-12}$ hydrocarbon chain.

28. The compound of claim 25, wherein L is an unsaturated C$_{5-10}$ hydrocarbon chain.

29. The compound of claim 25, wherein L is an unsaturated C$_{6-8}$ hydrocarbon chain.

30. The compound of claim 25, wherein L is an unsaturated hydrocarbon chain containing at least two double bonds.

31. The compound of claim 2, wherein the double bond is in trans configuration.

32. The compound of claim 2, wherein L is an unsaturated hydrocarbon chain containing at least two double bonds.

* * * * *